US00PP09335P

United States Patent [19]

VandenBerg

[11] Patent Number: Plant 9,335

[45] Date of Patent: Oct. 17, 1995

[54] CHRYSANTHEMUM PLANT NAMED 'MOBILE'

[75] Inventor: Cornelis P. VandenBerg, Salinas, Calif.

[73] Assignee: Yoder Brothers, Inc., Barberton, Ohio

[21] Appl. No.: 331,859

[22] Filed: Nov. 1, 1994

[51] Int. Cl.[6] ..... A01H 5/00

[52] U.S. Cl. ..... Plt./74.1

[58] Field of Search ..... Plt./74.1, 82.5, Plt./82.2

[56] References Cited

U.S. PATENT DOCUMENTS

P.P. 8,464 11/1993 VandenBerg ..... Plt./74.1

P.P. 8,465 11/1993 VandenBerg ..... Plt./74.1

*Primary Examiner*—Howard J. Locker

*Attorney, Agent, or Firm*—Foley & Lardner

[57] ABSTRACT

A Chrysanthemum plant named Mobile particularly characterized by its flat capitulum form; daisy capitulum type; bi-colored yellow and red ray floret color, with the bases of the ray florets being yellow, and the tips red, both colors overlapping in streaks; narrow petaloids which extend from the base of the ray floret around the disc; diameter across face of capitulum of 83 to 92 mm when fully opened, when grown as a pinched spray pot mum; photoperiodic flowering response to short days of 53 to 61 days; plant height with 14 to 15 long days after sticking unrooted cuttings, and with 1 to 3 applications of 2500 ppm B-9 SP, ranges from 23 to 33 cm when grown as a pinched pot mum with 4 cuttings in a 15 cm pot; branching pattern is spreading and prolific, each plant having 4 to 5 laterals after pinch; and recommended as a spray pot mum.

3 Drawing Sheets

The present invention comprises a new and distinct cultivar of Chrysanthemum, botanically known as *Dendranthema grandiflora,* and referred to by the cultivar name Mobile.

Mobile, identified as 6134 (90-168009), was originated from a cross made by Cornelis P. VandenBerg in a controlled breeding program in Salinas, Calif., in 1989.

The female parent of Mobile was an unnamed seedling identified as 1300 (83-750007) and described as a pot spray mum with a flat capitulum form; daisy capitulum type; bi-colored pink and white ray floret color; flowering response to short days in Salinas, Calif. of 50 to 58 days; plant height of 18 to 33 cm when grown with 15 to 16 long days after sticking unrooted cuttings prior to start of short days and 1 to 2 applications of 2500 ppm B-9 SP; and a branching pattern of 4 to 6 laterals developing after pinch. The female parent was discarded from all programs in April 1989, after completion of seed production.

The male parent of Mobile was the cultivar identified as Lucido, disclosed in U.S. Plant Pat. No. 6,586, and described as a pot spray mum with a flat capitulum form; daisy capitulum type; red ray floret color; diameter across face of capitulum of 70 to 83 mm when grown as a spray pot mum; flowering response to short days in Salinas, Calif. of 56 to 60 days; plant height of 23 to 30 cm when grown with 15 to 16 long days after sticking unrooted cuttings prior to start of short days, and 1 to 2 applications of 2500 ppm B-9 SP; and a branching pattern of 5 laterals developing after pinch. The ranges of measurements of Lucido are somewhat larger than the measurements disclosed in U.S. Plant Pat. No. 6,586 for Lucido. This is based on continuing flowering trials of Lucido.

Mobile was discovered and selected as one flowering plant within the progeny of the stated cross by Cornelis P. VandenBerg in May 1991, in a controlled environment in Salinas, Calif.

The first act of asexual reproduction of Mobile was accomplished when vegetative cuttings were taken from the initial selection in July 1991 in a controlled environment in Salinas, Calif., by technicians working under supervision of Cornelis P. VandenBerg.

Horticultural examination of controlled flowerings of successive plantings has shown that the unique combination of characteristics as herein disclosed for Mobile are firmly fixed and are retained through successive generations of asexual reproduction.

Mobile has not been observed under all possible environmental conditions. The phenotype may vary siginificantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Mobile, which, in combination, distinguish this Chrysanthemum as a new and distinct cultivar:

1. Flat capitulum form.
2. Daisy capitulum type.
3. Bi-colored yellow and red ray floret color, with the bases of the ray florets being yellow, and the tips being red, both colors overlapping in streaks.
4. Narrow petaloids extend from the base of the ray floret around the disc.
5. Diameter across face of capitulum of 83 to 92 mm when fully opened, when grown as a pinched spray pot mum.
6. Photoperiodic flowering response to short days of 53 to 61 days.
7. Plant height, with 14 to 15 long days after sticking unrooted cuttings and with 1 to 3 applications of 2500 ppm B-9 SP, ranges from 23 to 33 cm when grown as a pinched pot mum with 4 cuttings in a 15 cm pot.
8. Branching pattern is spreading and prolific, each plant having 4 to 5 laterals after pinch.
9. Recommended as a spray pot mum.

The accompanying photographic drawings show typical inflorescence and leaf characteristics of Mobile, with the colors being as nearly true as possible with illustrations of this type.

Sheet 1 is a color photograph of Mobile grown as a pinched spray pot mum with 4 cuttings in a 15 cm pot.

Sheet 2 is a black and white photograph of three views of the inflorescence of Mobile.

Sheet 3 is a black and white photograph showing the upper and under sides of the leaves of Mobile at 3 stages of development (mature, intermediate and immature). In sheets 2 and 3 a measuring tape in centimeters has been added.

No commercial cultivars known to the inventor are similar in ray floret color, with the ray floret color of Mobile being a unique bi-colored yellow and red. Most similar of the commercial varieties is the parent cultivar Lucido. Reference is made to attached Chart A, which compares certain characteristics of Mobile to the same characteristics of Lucido.

Similar traits are capitulum form and type and recommended use as a spray pot mum. Flowering response to short days of Mobile and Lucido is comparable. The ray floret color of Mobile is a unique yellow and red bi-color, while the ray floret color of Lucido is solid red. Mobile has a larger diameter of capitulum and a taller plant height, requiring more B-9 SP to attain commercial plant height than Lucido. The branching pattern of both cultivars is comparable, although Mobile produces one less lateral compared to Lucido.

In the following description color references are made to The Royal Horticultural Society Colour Chart. The color values were determined on plant material grown as a pinched spray pot mum in Salinas, Calif. on Aug. 10, 1994.

Classification:

*Botanical.*—*Dendranthema grandiflora* cv Mobile.

*Commercial.*—Daisy spray pot mum.

INFLORESCENCE

A. Capitulum:

*Form.*—Flat.

*Type.*—Daisy.

*Diameter across face.*—83 to 92 mm when fully opened.

B. Corolla of ray florets:

*Color (general tonality from a distance of three meters).*—Bi-colored yellow and red, with the bases of the ray florets being yellow and the tips red. The yellow bases show red streaking and the red tips show yellow streaking.

*Color (upper surface).*—Base 9A, streaked with 46A. Tip closet to 46A, streaked with 9A.

*Color (under surface).*—9B at base to 181A at tip.

*Shape.*—Straight, flat, rounded apex. Many ray florets develop long, narrow petaloids at the base, visible around the disc.

C. Corolla of disc florets:

*Color (mature).*—14B.

*Color (immature).*—144C.

D. Reproductive organs:

*Androecium.*—Present on disc florets only; moderate pollen.

*Gynoecium.*—Present on both ray and disc florets.

PLANT

A. General appearance:

*Height.*—23 to 33 cm when grown as a pinched pot mum with four cuttings in a 15 cm pot with 14 to 15 long days after direct sticking unrooted cuttings prior to start of short days, and 1 to 3 applications of 2500 ppm B-9 SP.

*Branching pattern.*—Spreading and prolific, with 4 to 5 laterals after pinch.

B. Foliage:

*Color (upper surface).*—147A.

*Color (under surface).*—147B.

*Shape.*—See photograph.

CHART A
COMPARISON OF MOBILE AND LUCIDO

| CHARACTERISTIC | MOBILE | LUCIDO |
|---|---|---|
| Ray floret color | Bi-colored yellow and red | Red |
| Capitulum form and type | Flat daisy | Flat daisy |
| Diameter across face of capitulum | 83 to 92 mm | 70 to 83 mm |
| Flowering response | 53 to 61 days | 56 to 60 days |
| Plant height with 14 to 17 long days | 23 to 33 cm | 23 to 30 cm |
| Branching pattern | 4 to 5 laterals | 5 laterals |
| Recommended as | Spray pot mum | Spray pot mum |

COMPARISONS MADE OF PLANTS GROWN AS PINCHED SPRAY POT MUMS IN SALINAS, CALIFORNIA

I claim:

1. A new and distinct Chrysanthemum plant named Mobile, as described and illustrated.

* * * * *

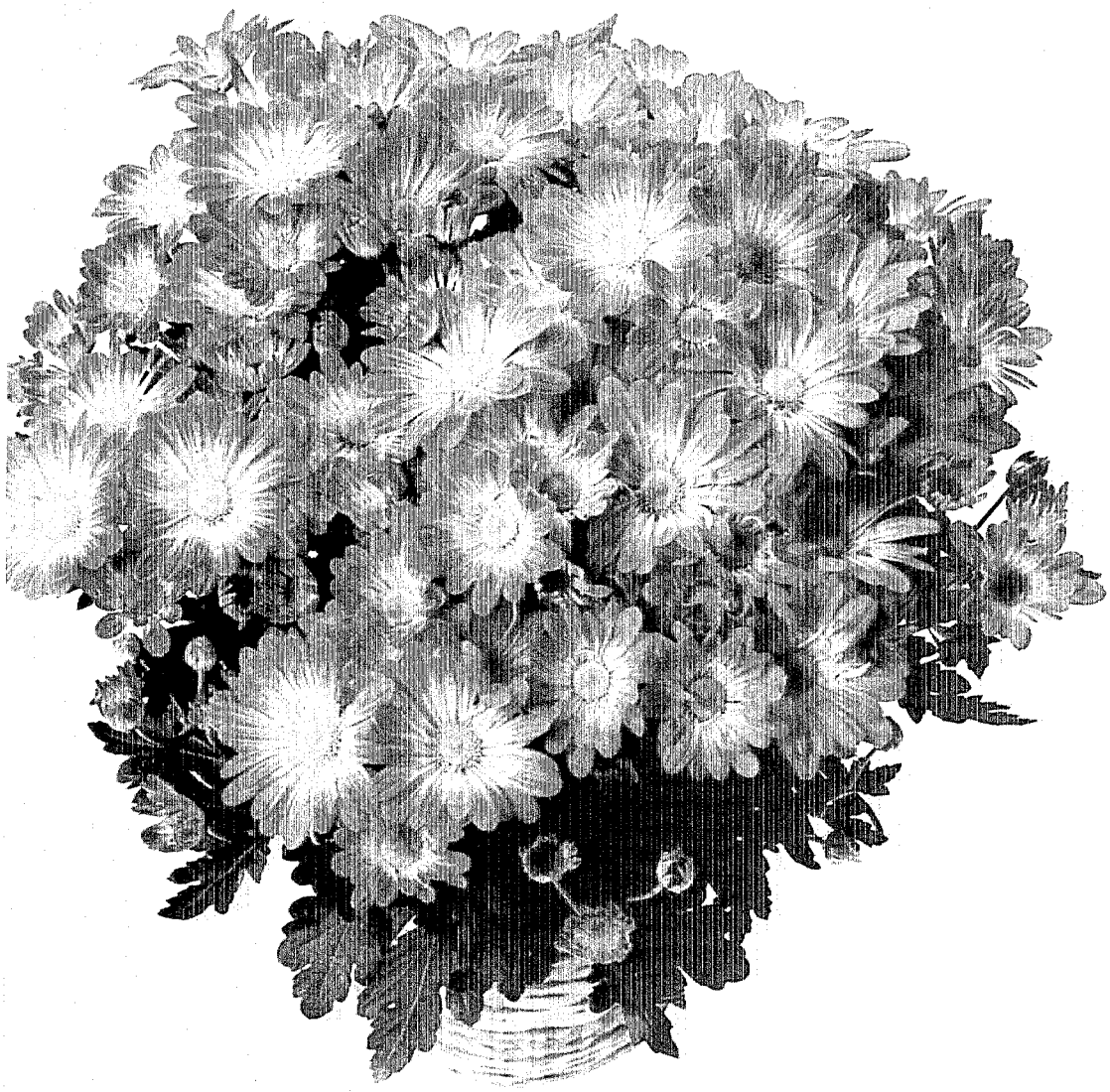

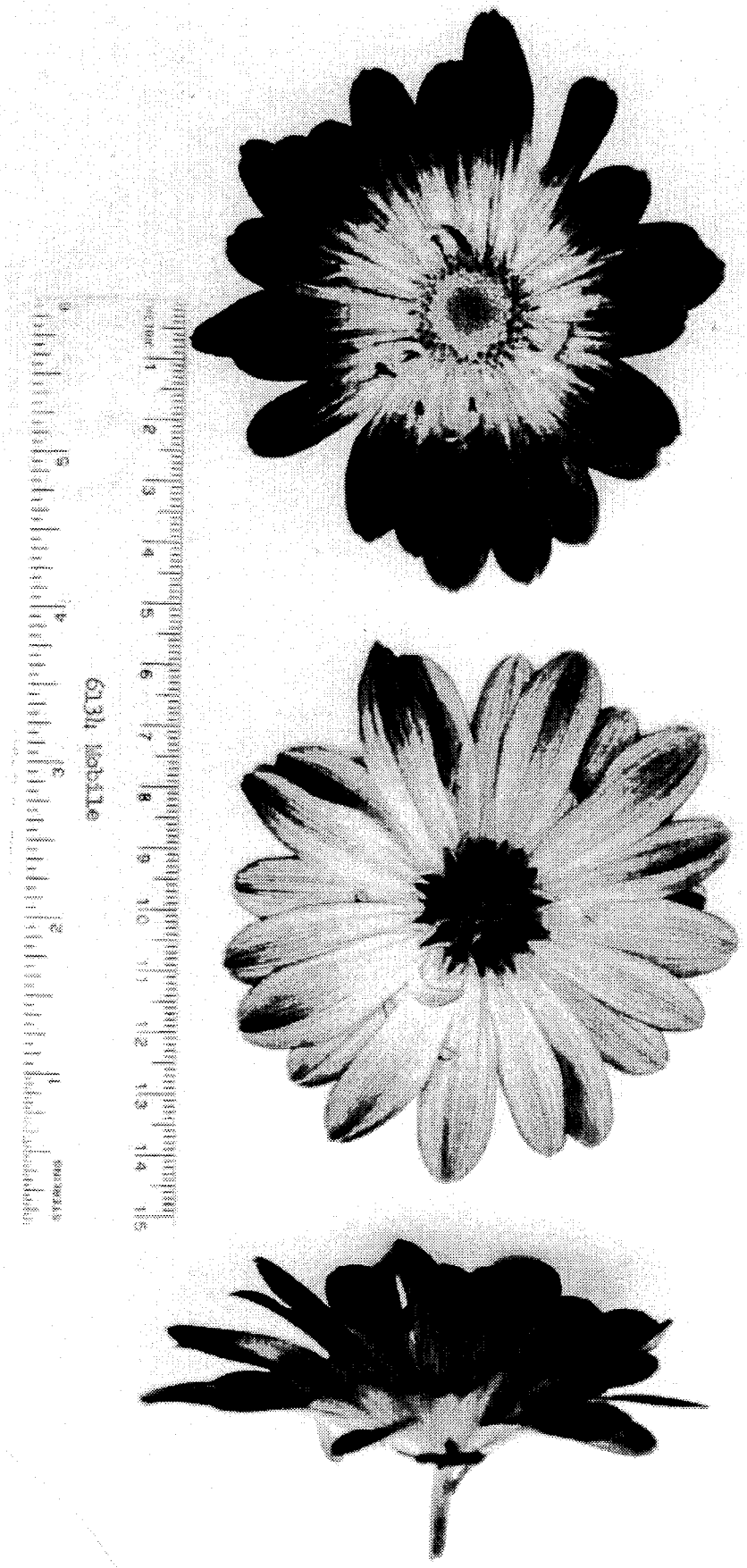
613h Mobile

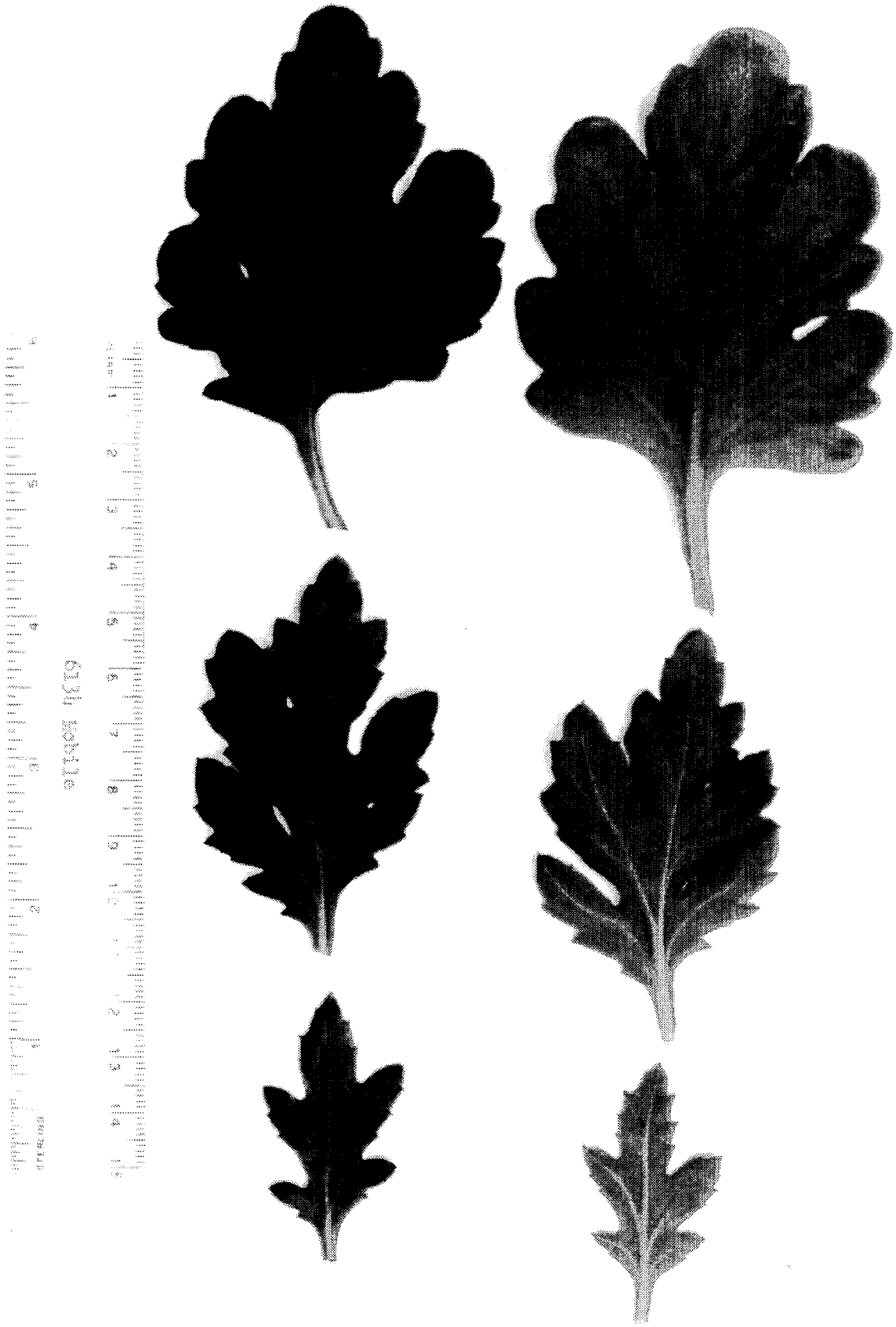
GLOW BORDER